United States Patent [19]

Fischell

[11] Patent Number: 4,730,607
[45] Date of Patent: Mar. 15, 1988

[54] STIFFENER CYLINDER FOR AN INFLATABLE PENILE ERECTION DEVICE

[76] Inventor: Robert E. Fischell, 1027 McCeney Ave., Silver Spring, Md. 20901

[21] Appl. No.: 772,734

[22] Filed: Sep. 5, 1985

Related U.S. Application Data

[63] Continuation-in-part of Ser. No. 642,244, Aug. 20, 1984, abandoned.

[51] Int. Cl.$^4$ ............................................. A61F 2/26
[52] U.S. Cl. ...................................................... 128/79
[58] Field of Search ........................................... 128/79

[56] References Cited

U.S. PATENT DOCUMENTS

| | | | |
|---|---|---|---|
| 2,538,136 | 1/1951 | Twachtman | 128/79 |
| 4,009,711 | 3/1977 | Uson | 128/79 |
| 4,201,202 | 5/1980 | Finney et al. | 128/79 |
| 4,235,227 | 11/1980 | Yamanaka | 128/79 |
| 4,267,829 | 5/1981 | Burton et al. | 128/79 |
| 4,318,396 | 3/1982 | Finney et al. | 128/79 |
| 4,360,010 | 11/1982 | Finney | 128/79 |
| 4,392,562 | 7/1983 | Burton et al. | 128/79 |
| 4,399,811 | 8/1983 | Finney et al. | 128/79 |
| 4,399,812 | 8/1983 | Whitehead | 128/79 |
| 4,407,278 | 10/1983 | Burton et al. | 128/79 |
| 4,429,689 | 2/1984 | Yanong | 128/79 |
| 4,628,912 | 12/1986 | Fischell | 128/79 |

FOREIGN PATENT DOCUMENTS

| | | | |
|---|---|---|---|
| 0051420 | 5/1982 | European Pat. Off. | |
| 0000302 | 3/1980 | PCT Int'l Appl. | 128/79 |
| 2160777 | 1/1986 | United Kingdom. | |

Primary Examiner—Gene Mancene
Assistant Examiner—Cary E. Stone
Attorney, Agent, or Firm—Fleit, Jacobson, Cohn & Price

[57] ABSTRACT

Disclosed is an improved stiffener cylinder for use as part of a penile erection device. The cylinder is constructed with one or more bellows-like folds that permit significant elongation and also eliminate localized cylinder buckling. Further, the cylinder is constructed with greater vertical expansion capability than horizontal expansion capability so that, when two of the cylinders are utilized in the penis in side-by-side relationship, the penis achieves a generally circular cross section in the erect state.

36 Claims, 6 Drawing Figures

U.S. Patent  Mar. 15, 1988  4,730,607
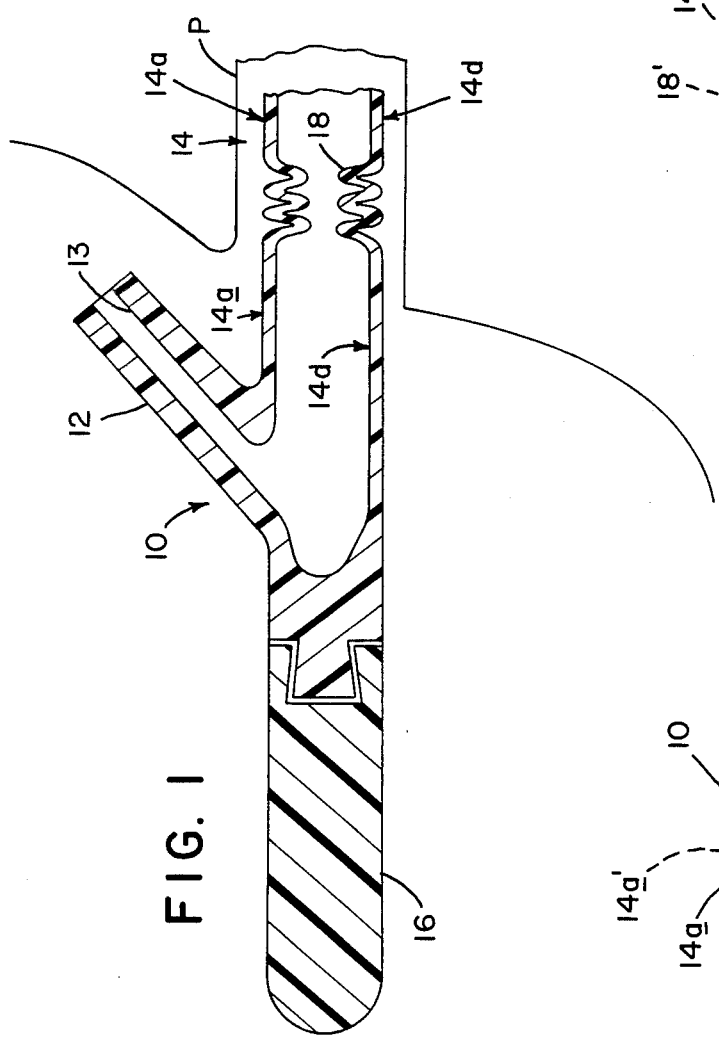
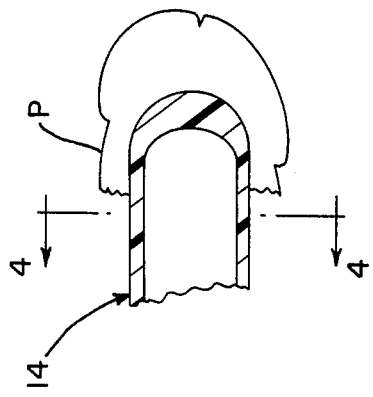
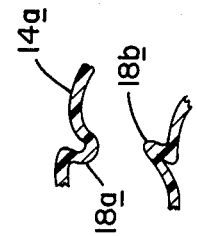
FIG. 2
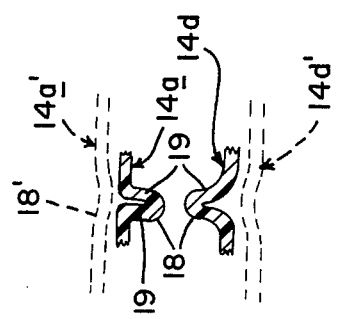
FIG. 3
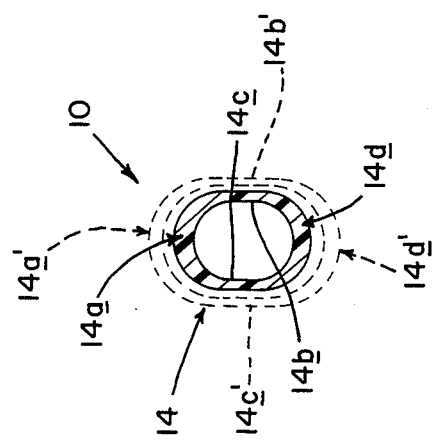
FIG. 4

STIFFENER CYLINDER FOR AN INFLATABLE PENILE ERECTION DEVICE

This is a continuation-in-part of Ser. No. 642,244 filed Aug. 20, 1984, now abandoned.

BACKGROUND OF THE INVENTION

1. Field of the Invention

This invention relates generally to the field of inflatable penile erection devices, and more specifically relates to an improved stiffener cylinder which is implanted into the corpus cavernosum of the penis.

2. Description of the Prior Art

There is an increasing amount of activity in the field of penile erection devices to aid the male suffering the affliction of erectile impotence. See, for example, copending U.S. patent application Ser. No. 476,931, now U.S. Pat. No. 4,559,931 entitled "Manually Actuated Fully Implantable Penile Erection Device." In this and other devices, fluid-actuated stiffener cylinders are implanted in each of the corpora cavernosa, and serve to effect the erect state when filled with fluid and to effect the flaccid state when relieved of fluid.

Present stiffener cylinders for inflatable penile erection devices have several serious deficiencies. One such deficiency is that they do not extend in length to any significant degree in the erect state. For example, these devices extend only by approximately 0.5% in going from the flaccid to the erect state, an almost imperceptible length change. A second deficiency is that in the flaccid state, the cylinders buckle where the pendulous portion enters the body. This could lead to cracking and leakage of fluid through the cylinders after several years of flexing.

A third deficiency is related to the implantation of two cylinders in the corpora cavernosa of the penis. The cylinders are circular in cross section and retain their circular shape when they expand. Because these cylinders are mounted side by side in the penis, when they are inflated, the pendulous portion of the penis assumes a flattened shape which is not physiologically equivalent to the generally circular cross section of the normally erect penis.

The U.S. Pat. No. 4,267,829 to Burton et al (FIG. 4) discloses a corrugated cloth material sandwiched between two elastomer cylinders as a structure for a penile cylinder. Although the corrugated cloth does allow some longitudinal expansion, while intentionally disallowing radial expansion, because the corrugations of the cloth are confined between two elastomer cylinders, longitudinal expansion is extremely restricted and the buckling phenomenon at the base of the pendulous portion of the penile cylinder is still present. Thus, the Burton et al patent does not disclose a device or method for obtaining a significantly longer length of the penis during erection, does not solve the problem of excessive stress at the point where the cylinder buckles in its flaccid state, and still produces a flattened shape when two cylinders in side-by-side relationship are inflated to an erect state.

SUMMARY OF THE INVENTION

In view of the aforementioned deficiencies in known stiffener cylinders, it is highly desirable to provide an improved cylinder that achieves a higher degree of physiologic normalcy than present cylinders by effecting a perceptible length change and permitting the penis to assume a generally circular cross section when erect. It also is desirable to improve upon present cylinders by providing a cylinder which is free from localized areas of stress.

Accordingly, an object of the present invention is to provide a stiffener cylinder whereby the penis attains considerably greater length in the erect state as compared to the flaccid state.

Another object of the present invention is to provide a means for eliminating the buckling of the stiffener cylinder where it enters the body, thus increasing the useful life of the cylinder.

Still another object of the present invention is to provide a stiffener cylinder with a non-circular, essentially elliptical cross section which expands to a greater extent in the vertical direction than in the horizontal direction so that the penis in the erect state is more physiologically circular in its cross section.

To accomplish the objects of growth in the lengthwise direction and elimination of localized stress, the stiffener cylinder of the present invention utilizes one or more folds at the base of the pendulous portion which elongate considerably when the cylinder fluid pressure is increased to obtain the erect state, and which, when the penis is in the flaccid state, allow bending without buckling. Furthermore, locating such folds at the base of the pendulous portion makes it possible to accommodate a physiologically normal bend of the penis in the flaccid state.

To accomplish the object of obtaining a circular cross section of the penis when in the erect state, each of the two stiffener cylinders may be made with a vertically elongated cross section and with thicker sections of elastomer in the top and bottom portions than in the sides. Thus, when the cylinder expands under increased internal fluid pressure (i.e., during the erect state), the cross section of the cylinder increases more in the vertical dimension than it does in the horizontal dimension. Hence, with two such cylinders mounted horizontally side-by-side (i.e., with adjacent vertical walls) the penis assumes an essentially circular cross section in the erect state rather than the less physiologic flattened state exhibited by using devices of the prior art.

A second manner of obtaining a stiffener cylinder which expands elliptically is to utilize a cylinder which is vertically elliptical in cross section, of essentially uniform wall thickness, and which has a horizontal elastomer septum molded into it at its center so as to join opposite side portions of the cylinder. The horizontal septum also defines upper and lower fluid-receiving chambers which are in fluid communication with one another by means of at least one opening defined by the septum. With this construction, both the top and bottom chambers can be made to expand more vertically as compared to horizontally. Thus, two such cylinders mounted horizontally side-by-side will provide a physiologically normal, circular cross section for the erect penis.

These and other objects of the invention, the advantages thereof, and the details of construction, will become more readily apparent when reference is made to the following description, taken in conjunction with the accompanying drawings.

BRIEF DESCRIPTION OF THE DRAWINGS

FIG. 1 is a longitudinal cross-sectional view of one form of an improved elliptical stiffener cylinder in a horizontal, but flaccid condition.

FIG. 2 is a fragmentary cross-sectional view showing a single fold of the pendulous portion of the cylinder as it is bent downwardly in the flaccid state.

FIG. 3 illustrates the fold of FIG. 2, showing the flaccid state in solid lines and the erect state in dotted lines.

FIG. 4 is a cross-sectional view of the stiffener cylinder, taken along the line 4—4 of FIG. 1, illustrating the provision of thin side walls and comparatively thick top and bottom sections.

DETAILED DESCRIPTION OF THE DRAWINGS

Figure 6:
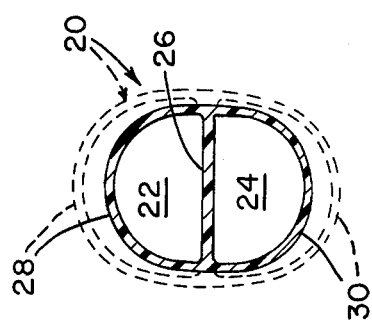
FIG. 6 is a cross-sectional view of the stiffener cylinder of FIG. 5, taken along the line 6—6 in that figure, which utilizes a centered, horizontal elastomer septum to provide more vertical as compared to horizontal displacement when the cylinder is pressurized.

In FIG. 1, the improved stiffener cylinder is shown generally at 10, as it would appear in the corpus cavernosum of the penis P of the human male. One such cylinder 10 is implanted in each of the two corpora cavernosa of the penis P. The cylinder 10 has an inlet section 12 which is connected at its interior surface 13 to a source of fluid (not shown). The addition of fluid under pressure causes the cylinder 10 to assume the erect state; the removal of fluid reduces the pressure and causes a return to the flaccid state.

Specific methods and apparatus for the addition and removal of fluid, and the overall cooperation of elements employed in penile erection devices of the type contemplated herein, are described in the aforementioned U.S. patent application Ser. No. 476,931.

The cylinder 10 has an inflatable pendulous portion 14 that is contained within the penis P, and a separate root portion 16. The pendulous portion 14 has an upper cylindrical section 14a, a lower cylindrical section 14d, and one or more folds 18 located at the base of the pendulous portion 14 of the penis P. FIG. 1 shows the shape of three such folds 18 when the penis P is flaccid but held out in a horizontal position. These folds 18 are generally in the shape of an extensible bellows with each fold corresponding to a single convolution of the bellows.

FIG. 2 shows the shape of a single fold 18 when the penis is bent downwardly from its base, which occurs normally in the flaccid state. Thus, the upper fold 18a is partially opened and the lower fold 18b is partially compressed.

Because the fold 18 bends as shown in FIG. 2, the cylinder 10 will not buckle when the penis is bent downwardly in adopting its normal flaccid state. This should result in a longer implant life for the cylinder 10 because the pendulous portion 14 will not be unduly stressed at its base because of buckling as is the case with existing prior art cylinders. Specifically, the prior art cylinders are without means which allow the upper portion of the cylinder to remain partially extended during bending without putting undue stress on a buckled lower portion. Such buckling eventually could cause the cylinder to crack at the stress points resulting in leakage of fluid into pendulous tissue and rendering the penile erection device inoperative.

In FIG. 3, the solid lines show one fold 18 in the flaccid (but unbent) configuration. The dotted lines, on the other hand, represent the condition when fluid pressure is increased within the pendulous portion 14 of the cylinder 10 (corresponding to the erect state). When in such condition, the fold 18 assumes the substantially straightened shape 18' without being placed in any significant tension, with the upper cylindrical section 14a adopting the shape as illustrated at 14a'. Because the fold 18 straightens when the cylinder 10 is in its erect state, the pendulous portion 14 assumes distinctly greater length during erection. Upon relief of fluid pressure, the fold 18 returns to the shape illustrated in solid lines in FIG. 3. The top and bottom of the fold 18 can be made distinctly thicker than the side walls thereof, if so desired, as is illustrated in FIG. 4 for the remainder of the cylinder 10.

The entire pendulous portion 14 of the cylinder, from the body to the tip, preferably is on the order of 15 centimeters in length. Each of the folds 18 preferably has a depth of 0.6 centimeters. It should be understood, however, that the length of the pendulous portion 14 and the depth of each fold 18 can be varied in order to adjust the characteristics of the device.

A fold depth of 0.6 cm permits a 1.2 cm per fold elongation of the pendulous portion 14, less the thickness of such a fold, as fluid pressure causes the cylinder 10 to assume the erect state. The thickness of a fold 18 is represented by the sum of the thickness of each of the two cylinder sections 19 (FIG. 3) which come together to form the fold, i.e., two sections of 0.1 cm thickness each yield a fold thickness of 0.2 cm. The centimeter per fold elongation is thus 1.2 cm minus 0.2 cm. If the pendulous portion 14 has three such folds 18, as shown in FIG. 1, with a depth of 0.6 cm, then the pendulous portion 14 is lengthened by 3.6 cm, less the 0.6 cm thickness of the folds, during the erect state.

For a pendulous portion 14 that is 15 centimeters in length, this elongation represents a 20% increase in pendulous length from the flaccid to the erect state. With such 0.6 cm depth of the folds 18, the percentage increase in pendulous length is approximately 6.5% and 13% for 1 fold and 2 folds, respectively. Even if the depth of the folds 18 was reduced to 0.3 cm, a single fold would increase the length of the cylinder by on the order of 3%. Since present cylinders permit only a fraction of one percent increase in pendulous length, the objective of providing a pendulous portion 14 with distinctly greater length during erection is accomplished even when the cylinder 10 is built with only one relatively shallow fold.

FIG. 4 shows the cross section of the pendulous portion 14 of the stiffener cylinder 10 at section line 4—4 of FIG. 1. In this view, the solid lines represent the flaccid state and the dotted lines represent the erect state. The vertical walls 14b and 14c are distinctly thinner and longer than the thicker and shorter top section 14a and the bottom section 14d, with the vertical walls and the top and bottom sections being symmetrical in cross section about perpendicular axes of the pendulous portion 14. Thus, when fluid pressure is increased within the confines of the cylinder 10, the thin walls 14b and 14c stretch and elongate vertically to a significant degree, and expand horizontally only slightly to positions 14b' and 14c' as shown by the dotted lines in FIG. 4. In contrast, the top section 14a and the bottom section 14d expand vertically a significant amount, but do not appreciably elongate horizontally.

This differential expansion and elongation results in less outward movement of the vertical walls 14b and 14c than of the top section 14a and the bottom section 14d when the cylinder 10 is pressurized. Hence, the ratio of the vertical dimension to the horizontal dimension of the pendulous portion 14 of the cylinder 10 increases from the flaccid state (shown by solid lines in FIG. 4) to the erect state (shown by dotted lines in FIG. 4). Because there are two such side-by-side cylinders 10 in the corpora cavernosa of the penis P, this design of the cylinders 10 causes the penis to assume a more circular cross section than is the case with the prior art, where both cylinders are circular in cross section and maintain that cross section as they expand. It also should be noted that the improved stiffener cylinders 10 accomplish two objectives relative to the shape and size of their cross section. They provide a physiologically circular cross section for the erect penis P, and provide a means whereby the erect penis becomes thicker and increases in girth.

Typical dimensions for an uninflated cylinder 10 are on the order of 0.8 to 1.0 cm from the outside of one vertical side wall 14b to the outside of the other vertical side wall 14c, and on the order of 1.3 to 1.4 cm from the top of the top section 14a to the bottom of the bottom section 14d. The respective thicknesses of the vertical side walls 14b and 14c, and the horizontal top and bottom sections 14a and 14d, are 0.02 cm and 0.1 cm. when inflated, the outside distance between side walls 14b' and 14c' increases about 0.1 cm to on the order of 0.9 to 1.1 cm, and the outside distance between top section 14a' and bottom section 14d' increases about 0.2 cm to on the order 1.5 to 1.6 cm. The magnitude of these dimensional increases depends upon the durometer of the elastomer material used in the stiffener cylinders 10. A durometer on the order of 35 to 50 would be typical for applications such as this.

Although the folds 18 are shown in FIG. 1 as being located at the base of the pendulous portion 14 of the cylinder 10, one or more of the folds could be located elsewhere along the length of the cylinder. However, it is preferable to locate at least one fold 18 at the pendulous base to permit the pendulous portion 14 to bend naturally without the creation of stress points at the lower portion of the base.

Figure 5:
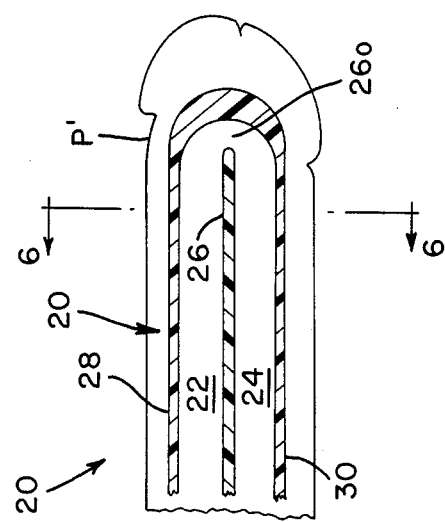
FIG. 5 is a partial longitudinal cross-sectional view of the distal portion of another form of an improved elliptical stiffener cylinder in a horizontal but flaccid condition.

FIG. 5 shows the distal portion of the longitudinal section of a second embodiment of an elliptical cylinder 20 that would provide a circular cross section of a penis P' when two such cylinders 20 are mounted side-by-side and then expanded. As shown in FIG. 6, the elliptical cylinder 20 utilizes an upper chamber 22 that is separated from a lower chamber 24 by a horizontal septum 26. The upper chamber 22 has an upper wall 28 and the lower chamber 24 has a lower wall 30. The thickness of both of the walls 28 and 30, and of the septum 26, is essentially uniform, approximately 0.03 cm. Typical outside dimensions of the uninflated cross section of the cylinder 20 would be 1.4 cm high by 1.0 cm in width. The septum 26 may terminate in spaced relationship to the tip of the cylinder 10, to define an opening 32, as shown in FIG. 5, or it may have small holes (not shown) therein, so as to provide fluid communication between the upper chamber 22 and the lower chamber 24.

It is the nature of thin walled, elliptically-shaped, elastomer cylinders that they tend to become circular when pressurized. Because of the horizontal septum 26, each chamber 22 and 24 will separately try to become essentially circular in configuration when pressurized, as illustrated by dashed lines in FIG. 6. Thus, because the uninflated dimensions of each chamber 22 and 24 are approximately 0.7 cm high by 1.0 cm wide, as noted above, when the chambers are pressurized, each will tend to approach a circular or round cross section as a result of an increase in the 0.7 cm dimension, with substantially less change in the 1.0 cm dimension at the septum 26. This will result in a greater expansion of the elliptical cross section 20 in the vertical direction as compared to the horizontal direction.

Thus, when two elliptical cylinders 20, as shown in FIGS. 5 and 6, are placed side-by-side and pressurized, they will cause the erect penis P' to have a circular cross section, which is the desired result. Another advantage of the embodiment of FIGS. 5 and 6 is that the horizontal septum 26 has very little stiffness and therefore, in the flaccid state, the penis P' will indeed be extremely flaccid.

Although a large variety of elastomer materials could be satisfactory for the stiffener cylinders 10 and 20, a medical grade silicone rubber or a polyethylene is preferred.

Various other modifications, adaptations and alternative designs are, of course, possible in light of the above teachings. Therefore, it should be understood that within the scope of the appended claims, the invention may be practiced otherwise than as specifically described herein.

What is claimed is:

1. A stiffener cylinder for a penile erection device, comprising:
    an elongated flexible pendulous portion having a wall with an outer surface and an inner surface defining an interior, said pendulous portion having an erect state when said interior is at a first pressure and having a flaccid state when said interior is at a second pressure lower than said first pressure; and
    elongation means defining a portion of the wall of said pendulous portion, including portions of the inner and outer surfaces of the wall, for increasing the length of said pendulous portion when in said erect state and for decreasing the length of said pendulous portion when in said flaccid state, said elongation means being capable of elongation to increase the length of said pendulous portion without being placed in any significant tension.

2. The stiffener cylinder as in claim 1, wherein said elongation means comprises a bellows.

3. The stiffener cylinder as in claim 2, wherein said bellows is located at a base of the pendulous portion.

4. The stiffener cylinder as in claim 2, wherein said bellows has one to three convolutions.

5. The stiffener cylinder as in claim 2, wherein the depth of the bellows is on the order of 0.3 cm.

6. The stiffener cylinder as in claim 2, wherein the depth of the bellows is on the order of 0.6 cm.

7. The stiffener cylinder as in claim 1, wherein the pressure within the cylinder interior is developed by a fluid.

8. The stiffener cylinder as in claim 1, wherein said elongation means lengthens the pendulous portion by at least 3%.

9. The stiffener cylinder as in claim 1, and further comprising a root portion attached to said pendulous portion at a base portion thereof.

10. A stiffener cylinder for a penile erection device, comprising:

an elongated flexible pendulous portion having a wall defining an interior, said pendulous portion having an erect state when said interior is at a first pressure and having a flaccid state when said interior is at a second pressure lower than said first pressure; and stress relief means in said pendulous portion for preventing buckling of localized areas of said pendulous portion when in said flaccid state, said stress relief means being capable of contraction in a lower portion of said pendulous portion and expansion in an upper portion of said pendulous portion, when said pendulous portion is moved into said flaccid state, and said stress relief means also serving to lengthen said pendulous portion.

11. The stiffener cylinder as in claim 10, wherein said stress relief means comprises a bellows.

12. The stiffener cylinder as in claim 11, wherein said bellows is located at a base of the pendulous portion.

13. The stiffener cylinder as in claim 11, wherein said bellows has one to three convolutions.

14. The stiffener cylinder as in claim 11, wherein the depth of the bellows is on the order of 0.3 cm.

15. The stiffener cylinder as in claim 11, wherein the depth of the bellows is on the order of 0.6 cm.

16. The stiffener cylinder as in claim 10, wherein the pressure within the cylinder interior is developed by a fluid.

17. The stiffener cylinder as in claim 10, and further comprising a root portion attached to said pendulous portion at a base portion thereof.

18. A stiffener cylinder for a penile erection device, comprising:

an elongated flexible pendulous portion having a wall defining an interior, said pendulous portion having an erect state when said interior is at a first pressure and having a flaccid state when said interior is at a second pressure lower than said first pressure;

elongation means in said pendulous portion for increasing the length of said pendulous portion when in said erect state and for decreasing the length of said pendulous portion when in said flaccid state, said elongation means being capable of elongation to increase the length of said pendulous portion without being placed in any significant tension; and stress relief means in said pendulous portion for preventing buckling of localized areas of said pendulous portion when in said flaccid state, said stress relief means being capable of contraction in a lower portion of said pendulous portion and expansion in an upper portion of said pendulous portion, when said pendulous portion is moved into said flaccid state.

19. The stiffener cylinder as in claim 18, wherein the pressure within the cylinder interior is developed by a fluid.

20. The stiffener cylinder as in claim 18, wherein said elongation means lengthens the pendulous portion by at least 3%.

21. The stiffener cylinder as in claim 18, and further comprising a root portion attached to said pendulous portion at a base portion thereof.

22. A stiffener cylinder for a penile erection device, of a type to be mounted in the corpora cavernosa of a penis in side-by-side relationship with a stiffener cylinder of the same construction, comprising:

an elongated flexible pendulous portion having a wall defining an interior, said pendulous portion having an erect state when said interior is at a first pressure and having a flaccid state when said interior is at a second and lower pressure;

said wall having extendable side portions and extendable top and bottom portions, the side portions and the top and bottom portions being essentially symmetrical in cross-section about perpendicular axes of the pendulous portion; and said wall extending more in one direction corresponding to one of the perpendicular axes of said pendulous portion than in a second direction corresponding to a second one of the perpendicular axes of said pendulous portion, when said pendulous portion goes from said flaccid state to said erect state, such that said pendulous portion has an elliptical configuration in said eret state.

23. The stiffener cylinder as in claim 22, wherein said top and bottom portions are thicker than said side portions.

24. The stiffener cylinder as in claim 22, wherein said top and bottom portions are shorter than said side portions.

25. The stiffener cylinder as in claim 22, and further comprising elongation means in said pendulous portion for increasing the length of said pendulous portion when in said erect state and for decreasing the length of said pendulous portion when in said flaccid state.

26. The stiffener cylinder as in claim 25, and further including stress relief means in said pendulous portion for preventing buckling of localized areas of said pendulous portion when in said flaccid state.

27. The stiffener cylinder as in claim 22, and further including stress relief means in said pendulous portion for preventing buckling of localized areas of said pendulous portion when in said flaccid state.

28. The stiffener cylinder as in claim 22, and further comprising a root portion attached to said pendulous portion at a base portion thereof.

29. A stiffener cylinder for a penile erection device, comprising:

an elongated flexible pendulous portion having a wall defining an interior, said pendulous portion having an erect state when said interior is at a first pressure and having a flaccid state when said interior is at a second and lower pressure;

said wall having extenable side portions and extendable top and bottom portions, the side portions and the top and bottom portions being esentially symmerical in cross section about perpendicular axes of the pendulous portion;

said wall extending more in one direction corresponding to one of the perpendicular axes of said pendulous portion than in a second direction corresponding to a second one of the perpendicular axes of said pendulous portion, when said pendulous portion goes from said flaccid state to said erect state, such that said pendulous portion has an elliptical configuration in said erect state; and said top, bottom and side portions being of essentially uniform thickness, and a planar septum joining said side portions to limit outward expansion of the side portions in the plane of the septum.

30. The stiffener cylinder as in claim 29, wherein the planar septum defines fluid-receiving chambers in the stiffener cylinder on opposite sides of the septum.

31. The stiffener cylinder as in claim 30, wherein the fluid-receiving chambers are in fluid communication with one another through at least one opening defined by said septum.

32. A stiffener cylinder for a penile erection device, comprising:

an elongated flexible pendulous portion having a wall defining an interior, said pendulous portion having an erect state when said interior is at a first pressure and having a flaccid state when said interior is at a second pressure lower than said first pressure;

elongation means in said pendulous portion for increasing the length of said pendulous portion when in said erect state and for decreasing the length of said pendulous portion when in said flaccid state; and stress relief means in said pendulous portion for preventing buckling of localized areas of said pendulous portion when in said flaccid state, said elongation means and said stress relief means comprising a single structure including a bellows.

33. The stiffener cylinder as in claim 32, wherein said bellows is located at a base of the pendulous portion.

34. The stiffener cylinder as in claim 32, wherein said bellows has one to three convolutions.

35. The stiffener cylinder as in claim 32, wherein the depth of the bellows is on the order of 0.3 cm.

36. The stiffener cylinder as in claim 32, wherein the depth of the bellows is on the order of 0.6 cm.

* * * * *